US011512280B2

(12) United States Patent
Morishita

(10) Patent No.: US 11,512,280 B2
(45) Date of Patent: Nov. 29, 2022

(54) METHOD FOR CULTURING SPORE-FORMING BACTERIA, AND METHOD FOR PRODUCING USEFUL SUBSTANCE

(71) Applicant: SDS BIOTECH K.K., Tokyo (JP)

(72) Inventor: Yasuyuki Morishita, Chiyoda-ku (JP)

(73) Assignee: SDS BIOTECH K.K., Tokyo (JP)

( * ) Notice: Subject to any disclaimer, the term of this patent is extended or adjusted under 35 U.S.C. 154(b) by 529 days.

(21) Appl. No.: 16/339,807

(22) PCT Filed: Oct. 6, 2017

(86) PCT No.: PCT/JP2017/036433
§ 371 (c)(1),
(2) Date: Apr. 5, 2019

(87) PCT Pub. No.: WO2018/066686
PCT Pub. Date: Apr. 12, 2018

(65) Prior Publication Data

US 2020/0040300 A1 Feb. 6, 2020

(30) Foreign Application Priority Data

Oct. 7, 2016 (JP) ............................ JP2016-199429

(51) Int. Cl.
*C12N 1/20* (2006.01)
*C12P 17/14* (2006.01)
*C12R 1/07* (2006.01)

(52) U.S. Cl.
CPC ................ *C12N 1/20* (2013.01); *C12P 17/14* (2013.01); *C12R 2001/07* (2021.05)

(58) Field of Classification Search
CPC ... C12N 1/20; C12N 1/38; C12P 17/14; C12P 1/00; C12P 1/04; C12P 21/00; C12R 2001/07
See application file for complete search history.

(56) References Cited

U.S. PATENT DOCUMENTS 5,462,862 A * 10/1995 Groenen .............. C07K 14/375 435/43
2004/0043451 A1 3/2004 Yoneda et al.
2005/0266521 A1 12/2005 Yoneda et al.

FOREIGN PATENT DOCUMENTS

JP 2000-217567 A 8/2000
JP 3635638 B2 4/2005
JP 2006-129778 A 5/2006
JP 2007-195542 A 8/2007
JP 2007-236286 A 9/2007
JP 4338080 B2 9/2009

OTHER PUBLICATIONS

Cagri-Mehmetoglu et al. Production of polysaccharide and surfactin by Bacillus subtilis ATCC 6633 using rehydrated whey powder as the fermentation medium. J. Dairy Sci. (2012), 95 :3643-3649 (Year: 2012).*

David R. Lide, ed., CRC Handbook of Chemistry and Physics, Internet Version 2005, <http://www.hbcpnetbase.com>, CRC Press, Boca Raton, FL, 2005. (Year: 2005).*

Berbert-Molina et al. Kinetics of *Bacillus thuringiensis* var. *israelensis* growth on high glucose concentrations. J Ind Micriobiol Biotechnol (2008), 35, 1397-1404. (Year: 2008).*

Belton et al. Antibiotics produced by Bacillus licheniformis. J Gen Microbiol. (1949), 3(3), 400-9. (Year: 1949).*

Mansoor et al. Inhibition of Bacillus licheniformis spore growth in milk by nisin, monolaurin, and pH combinations. Journal of Applied Microbiology (1999), 86, 311-324. (Year: 1999).*

Levinson et al. Some Effects of Heat and Ionizing Radiation on Spores of Bacillus Megaterium. J Bacteriol. (1960), 80(4), 441-451 (Year: 1960).*

International Search Report dated Dec. 26, 2017 in PCT/JP2017/036433 filed Oct. 6, 2017.

Monteiro, S. M. S. et al., "Enhanced Spore Production of *Bacillus subtilis* Grown in a Chemically Defined Medium," Advances in Microbiology, vol. 4, Jun. 2014, pp. 444-454.

Basalp, A. et al., "Changes in Patterns of Alkaline Serine Protease and Bacilysin Formation Caused by Common Effectors of Sporulation in *Bacillus subtilis* 168," Current Microbiology, vol. 24, 1992, pp. 129-135.

Ochi, K. et al., "Effect of Antibiotics on Sporulation Caused by the Stringent Response in *Bacillus subtilis*," Journal of General Microbiology, vol. 129, Apr. 8, 1983, pp. 3709-3720.

Takahashi, I. et al., "Effects of various inhibitory agents on sporulation of *Bacillus subtilis*," Can. J. Microbiol, vol. 28, 1982, pp. 80-86.

Monteiro, S. M. et al., "A Procedure for High-Yield Spore Production by *Bacillus subtilis*," Biotechnol. Prog., vol. 21, 2005, pp. 1026-1031.

Tavares, M. B. et. al., "*Bacillus subtilis* Endospores at High Purity and Recovery Yields: Optimization of Growth Conditions and Purification Method," Curr Microbiol, vol. 66, 2013, pp. 279-285.

* cited by examiner

*Primary Examiner* — Sean C. Barron
(74) *Attorney, Agent, or Firm* — Oblon, McClelland, Maier & Neustadt, L.L.P.

(57) ABSTRACT

An object of the present invention is to provide a novel culturing method by which spores can be efficiently produced. The present invention further provides a method for culturing sporulating bacteria, comprising adding a sporulation-inhibiting substance into a medium for culturing sporulating bacteria, wherein the carbon content in the medium is 9.1 g/L or more, and preferably further comprising a step of adding a sporulation-accelerating substance to the medium.

14 Claims, No Drawings

METHOD FOR CULTURING SPORE-FORMING BACTERIA, AND METHOD FOR PRODUCING USEFUL SUBSTANCE

TECHNICAL FIELD

The present invention relates to a method for culturing sporulating bacteria.

BACKGROUND ART

Sporulating bacteria such as those of the genus *Bacillus* are used in various fields of production of enzymes and useful substances, production of fermented food, decomposition of organic matter, medicines for intestinal disorders, microbial pesticides and microbial fertilizers, for example.

The use of sporulating bacteria as medicines for intestinal disorders, microbial pesticides, or microbial fertilizers requires the addition of viable cells as an active component to the products, and cells in the form of spores with good durability are generally used therefor. Accordingly, a method for producing spores with higher efficiency has been required.

Sporulating bacteria grow when placed in an environment appropriate for the growth and form spores in vegetative cells when placed in an environment appropriate for sporulation. Since the number of spores will never exceed the number of original vegetative cells, at least two aspects exist for improving the productivity of spores, improvement in culture productivity for culturing vegetative cells and improvement in the rate of sporulation from vegetative cells.

Such an environment appropriate for growth is an environment where nutritive components are present in amounts sufficient for the growth of the relevant bacterial strain, and the volume of water, osmotic pressure, temperature, pH, oxygen concentration, and the like are within the ranges that allow the growth of the same.

Furthermore, a method for producing target metabolites with higher efficiency has been required for production of enzymes and useful substances. At least two aspects exist for improvement of the productivity of enzymes and useful substances, induction to a metabolic state in which a target substance is produced at a high level and maintenance of the state for a long time.

Conventionally, improvement in culture productivity for culturing vegetative cells and maintenance of a metabolic state in which metabolites are produced at high levels have been achieved through optimization of the above various conditions, particularly improvement of medium composition and improvement of the concentration.

There are many reports concerning technology for producing *Bacillus* bacterial spores at high levels, as illustrated in Non Patent Documents 1 to 3, for example, however, techniques employed in these reports are improvement of the compositions and that of the concentrations of media. Non Patent Document 3 of these documents reports the highest productivity, however, according to this document, the amount of a sugar to be used per liter of medium is about 100 g/L (including the amount to be fed), the medium used herein contains a very high concentration of the sugar. However, further increases in the concentration of the sugar causes harms such that a culture apparatus becomes unable to oxygenate due to the increased oxygen demand, nutritive components remain for a long time in the medium, leading to a decrease in sporulation rate, a prolonged time required for culturing, for example. Moreover, an increase itself in the concentration of nutritive components such as sugars may exhibit an effect of inhibiting the growth. Furthermore, when the concentration of vegetative cells is increased during culture, a mechanism, “quorum sensing” of detecting its own concentration and switching metabolisms, induces sporulation, and thus a phenomenon can take place such that even when the concentration of nutritive components is further increased, vegetative cells do not grow beyond a certain level.

As described above, there has been a limit to conventional techniques that involve increasing the concentration of nutritive components to be added to media to increase culture productivity.

Meanwhile, Patent Document 1 discloses a method for causing sporulation by lowering dissolved oxygen concentration after the growth of vegetative cells. Further, Patent Document 2 discloses a method for causing sporulation by continuing long-time culture after a carbon source is consumed completely. Furthermore, Patent Document 3 discloses a method for producing spores by defining the range of the phosphate concentration in the culture medium and the range of the oxygen supply and stirring rate as culture conditions. However, all of these techniques provide the conditions appropriate for sporulation of vegetative cells, and do not contribute to “high-concentration growth of vegetative cells” essential for drastic improvement of the productivity of spores.

Furthermore, Non Patent Document 4 discloses that the use of an antibiotic at a concentration lower than a growth-inhibiting concentration can inhibit *Bacillus* bacteria from forming spores during culturing, and the addition of decoyinine thereto can counteract the effect of inhibiting sporulation. However, the document also demonstrates that in such a medium (glucose concentration of 1%, and carbon content of 4.0 g/L in the medium) containing an antibiotic at such a low concentration as used in Patent Document 4, the concentration of the thus formed spores decreases depending on the concentration of the antibiotic added, so that this technology cannot be said as the one capable of contributing to the high-level production of spores.

There are multiple reports concerning technology for producing useful substances using *Bacillus* bacteria as illustrated in Patent Documents 4 and 5, for example, but both documents describe techniques for improving medium compositions and culture conditions. However, because of increased oxygen demand, growth inhibition by nutritive components, sporulation induction by quorum sensing, and the like as described above, there has been a limit to techniques for improving culture productivity by increasing the concentrations of medium components.

These Patent Documents further disclose methods for obtaining bacterial strains capable of producing target metabolites at high levels through the use of transformants or mutation, however, this alters the genetic traits of a wild-type strain, possibly resulting in a loss or a weakening of other useful properties.

PRIOR ART REFERENCES

Patent Documents

Patent Document 1: JP2007-236286A
Patent Document 2: JP2000-217567A
Patent Document 3: JP2007-195542A
Patent Document 4: JP3635638B
Patent Document 5: JP4338080B Non Patent Documents Non Patent Document 1: Biotechnology progress 2005, 21, 4, 1026-1031
Non Patent Document 2: Curr Microbiol 2013, 66, 279-285
Non Patent Document 3: Advances in Microbiology 2014, 4, 444-454
Non Patent Document 4: Journal of General Microbiology 1983, 129, 3709-3720

SUMMARY OF THE INVENTION

Problems to be Solved by the Invention

As described above, there has been a limit to conventional techniques for increasing the spore productivity of sporulating bacteria and the productivity of useful substances such as metabolites by increasing medium concentrations. Hence, an object of the present invention is to provide a novel culturing method using a new approach, by which spores and useful substances such as metabolites can be produced efficiently through improvement of the growth efficiency of vegetative cells during culture.

Means for Solving the Problems

As a result of intensive studies to address the above problems, the present inventor has discovered that the productivity of spores and that of useful substances such as metabolites can be significantly improved, compared with a case of adding no sporulation-inhibiting substance, by growing vegetative cells in the presence of a sporulation-inhibiting substance using a medium containing a high concentration of a carbon source, and then inducing sporulation. Therefore, the present inventor has completed the present invention.

The present invention is as follows:

[1] A method for culturing a sporulating bacterium, comprising culturing a sporulating bacterium in a medium to which a sporulation-inhibiting substance is added, wherein the medium has a carbon content of 9.1 g/L or more.

[2] The method for culturing a sporulating bacterium according to [1], wherein the sporulation-inhibiting substance is an enzyme inhibitor.

[3] The method for culturing a sporulating bacterium according to [1] or [2], wherein the sporulation-inhibiting substance is at least one substance selected from the group consisting of lincomycin, erythromycin, rifampicin, chloramphenicol, streptomycin, caffeine, caffeic acid, actinomycin, fusidic acid, lipiarmycin, puromycin, spectinomycin, tetracycline, and thiostreptone.

[4] The method for culturing a sporulating bacterium according to any one of [1] to [3], wherein the concentration of the sporulation-inhibiting substance is the same as or lower than the growth-inhibiting concentration of the substance at which the growth of the sporulating bacteria is inhibited.

[5] The method for culturing a sporulating bacterium according to any one of [1] to [4], wherein the concentration of the sporulation-inhibiting substance is 15 ppm or less.

[6] The method for culturing a sporulating bacterium according to any one of [1] to [5], comprising adding a sporulation-accelerating substance to the medium.

[7] The method for culturing a sporulating bacterium according to [6], wherein the sporulation-accelerating substance is added into the medium at a timing in a time period of from five hours to seventy hours after the start of culture.

[8] The method for culturing a sporulating bacterium according to [6] or [7], wherein the sporulation-accelerating substance is a nucleobase analogue, an organic acid, an amino acid, an ammonium compound, a nitric acid compound, a nitrous acid compound or a mineral.

[9] The method for culturing a sporulating bacterium according to any one of [6] to [8], wherein the sporulation-accelerating substance is at least one substance selected from the group consisting of decoyinine, mizoribine, mycophenol, 6-azauracil, lactic acid and a salt thereof, acetic acid and a salt thereof, butyric acid and a salt thereof, manganese, ammonium, calcium, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, ammonium lactate, and ammonium acetate.

[10] The method for culturing a sporulating bacterium according to any one of [6] to [9], wherein the sporulation-accelerating substance is added at a concentration of 10 ppm to 10,000 ppm to the medium.

[11] The method for culturing a sporulating bacterium according to any one of [1] to [10], wherein the sporulating bacterium is a *Bacillus* bacterium.

[12] The method for culturing a sporulating bacterium according to [11], wherein the *Bacillus* bacterium is selected from *Bacillus subtilis, Bacillus amyloliquefaciens, Bacillus pumilus, Bacillus simplex, Bacillus lentus, Bacillus laterosporus, Bacillus alvei, Bacillus popilliae, Bacillus licheniformis, Bacillus brevis, Bacillus stearothermophilus, Bacillus alcalophilus, Bacillus coagulans, Bacillus circulans, Bacillus siamensis, Bacillus lautus, Bacillus clausii, Bacillus megaterium, Bacillus thuringiensis, Bacillus cereus, Bacillus firmus, Bacillus velezensis, Bacillus pichinotyi, Bacillus acidocaldarius, Bacillus alkalicola, Bacillus azotoformans, Bacillus anthracis, Bacillus badius, Bacillus bataviensis, Bacillus cycloheptanicus, Bacillus aneurinilyticus, Bacillus migulanus, Bacillus abyssalis, Bacillus aestuarii, Bacillus polymyxa*, and *Bacillus* sp.

[13] A method for producing a useful substance, comprising producing a useful substance by using the culturing method according to any one of [1] to [12].

[14] The method for producing a useful substance according to [13], wherein the useful substance is a spore of the sporulating bacterium.

[15] The method for producing a useful substance according to [13], wherein the useful substance is a metabolite of the sporulating bacterium.

[16] The production method according to [15], wherein the metabolite is a cyclic lipopeptide.

[17] The production method according to [16], wherein the cyclic lipopeptide is at least one cyclic lipopeptide selected from the group consisting of iturin, surfactin, plipastatin, fengycin, bacillomycin, lichenysin, kurstakin, mycosubtilin, colistin, fusaricidin, paenibacterin, polymyxin, and pumilacidin.

Effect of the Invention

Sporulating bacteria switch metabolisms from the growth in the form of vegetative cells to sporulation through sensing of the depletion of nutrients and quorum sensing. The method of the present invention maintains the period of vegetative growth longer than usual through inhibition of metabolic switching toward sporulation independently from conventional techniques of increasing medium concentrations, achieving a higher concentration of vegetative cells and a higher concentration of metabolites. Furthermore, by addition of a sporulation-accelerating substance and removal of the inhibiting substance, and ensuring a sufficiently long culture period, the method enables the formation of spores, and can drastically increase the final spore productivity and the productivity of useful substances such as metabolites.

EMBODIMENTS FOR CARRYING OUT THE INVENTION

The method for culturing sporulating bacteria of the present invention comprises culturing a sporulating bacterium in a medium to which a sporulation-inhibiting substance is added, wherein the medium has a carbon content of 9.1 g/L or more.

The spores of sporulating bacteria and useful substances such as metabolites can be obtained with good productivity by using the method for culturing sporulating bacteria of the present invention.

In the present invention, the type of sporulating bacteria is not particularly limited, and examples thereof include *Bacillus* bacteria, *Paenibacillus* bacteria, *Geobacillus* bacteria, *Clostridium* bacteria, and *Sporosarcina* bacteria.

Examples of *Bacillus* bacteria are not particularly limited as long as they are bacteria classified as the genus *Bacillus*, and include *Bacillus subtilis, Bacillus amyloliquefaciens, Bacillus pumilus, Bacillus simplex, Bacillus lentus, Bacillus laterosporus, Bacillus alvei, Bacillus popilliae, Bacillus licheniformis, Bacillus brevis, Bacillus stearothermophilus, Bacillus alcalophilus, Bacillus coagulans, Bacillus circulans, Bacillus siamensis, Bacillus lautus, Bacillus clausii, Bacillus megaterium, Bacillus thuringiensis, Bacillus cereus, Bacillus firmus, Bacillus velezensis, Bacillus pichinotyi, Bacillus acidocaldarius, Bacillus alkalicola, Bacillus azotoformans, Bacillus anthracis, Bacillus badius, Bacillus bataviensis, Bacillus cycloheptanicus, Bacillus aneurinilyticus, Bacillus migulanus, Bacillus abyssalis, Bacillus aestuarii, Bacillus polymyxa*, and *Bacillus* sp.

Examples of *Paenibacillus* bacteria include *Paenibacillus macerans, Paenibacillus amylolyticus, Paenibacillus peoriate*, and *Paenibacillus elgii.*

Examples of *Geobacillus* bacteria include *Geobacillus thermoglucosidasius, Geobacillus caldoxylosilyticus*, and *Geobacillus stearothermophilus.*

Examples of *Clostridium* bacteria include *Clostridium butyricum, Clostridium kluyveri, Clostridium acetobutylicum, Clostridium aminobutyricum, Clostridium beijerinckii, Clostridium saccharoperbutylacetonicum, Clostridium thermocellum, Clostridium ljungdahlii*, and *Clostridium botulinum.*

Examples of *Sporosarcina* bacteria include *Sporosarcina pasteurii, Sporosarcina ureae, Sporosarcina psychrophila*, and *Sporosarcina* thermotolerans.

Sporulating bacteria such as *Bacillus* bacteria may be non-recombinant bacteria or recombinant bacteria, and are preferably bacteria carrying no antibiotic-resistant gene.

In the present invention, the term “useful substance(s)” refers to substances exhibiting bioactivity such as effects of accelerating animal and plant growth, bactericidal.bacteriostatic action, and effects of activating genes, industrially applicable substances such as various enzymes, lactic acids, and amino acids, and fermented products themselves to be used as food such as fermented soybeans and yogurt. Specific examples thereof include the spores of sporulating bacteria and the metabolites of *Bacillus* bacteria. The metabolites of *Bacillus* bacteria are active components other than viable cells, which are produced via culturing, and examples thereof include cyclic peptides having antibiotic activity and surface activity and enzymes such as protease and lipase.

Examples of a cyclic lipopeptide that is a metabolite of *Bacillus* bacteria include at least one cyclic lipopeptide selected from the group consisting of iturin, surfactin, plipastatin, fengycin, bacillomycin, lichenysin, kurstakin, mycosubtilin, colistin, fusaricidin, paenibacterin, polymyxin and pumilacidin.

A liquid medium to be used for culturing contains a carbon source and a nitrogen source. Examples of a catabolizable carbon source that can be catabolized by sporulating bacteria such as *Bacillus* bacteria include sugars (such as starch, glucose, lactose, glycerol, arabinose, ribose, xylose, galactose, fructose, mannose, inositol, mannitol, sorbitol, glucosamine, N-acetylglucosamine, cellobiose, maltose, sucrose, trehalose, and xylitol) or sugar-source raw materials, alcohols, organic acids, organic acid salts, alkanes or other general carbon sources. Examples of a catabolizable nitrogen source that can be catabolized by sporulating bacteria such as *Bacillus* bacteria include soybean-derived components, yeast-derived components, corn-derived components, animal and plant proteins and catabolites thereof, ammonium salts such as ammonium nitrate, ammonium sulfate, ammonium chloride, and ammonium acetate, ammonia, sodium nitrate, potassium nitrate, sodium glutamate, and urea.

The carbon content in the liquid medium to be used in the present invention is preferably 9.1 g/L or more, preferably 10.2 g/L or more, and more preferably 15 g/L or more. Further preferably, the carbon content is preferably 18 g/L or more.

The content of carbon that is a natural raw material among medium components can be roughly calculated as 40% by weight of the total sugar amount and 50% by weight of the total protein amount. The total sugar amount can be determined as reducing sugar concentration by Somogyi method after 2.5 hours of hydrolysis in acid at 100° C. The total protein amount can be roughly calculated by determining the total nitrogen amount by Kjeldahl method and then multiplying the amount by the conversion factor, 6.25.

When the concentration of a carbon source in a medium is low, sporulation is initiated as the carbon source is depleted. In this case, when a sporulation-inhibiting (delaying) substance is added, bacterial cells in the vegetative state are exposed to the depletion of nutritive components for a long time. Accordingly, death of vegetative cells is accelerated compared with a case where no sporulation-inhibiting substance is added, resulting in lowered culture productivity (Non Patent Document 4 falls under this case). On the other hand, when the concentration of a carbon source in a medium is sufficiently high, sporulation is initiated via quorum sensing or the like, as vegetative cells grow. In this case, when a sporulation-inhibiting substance is added, the vegetative growth period is longer than that in a case where no sporulation-inhibiting substance is added. In general, vegetative cells grow to a degree significantly greater than the density of cells that form spores via quorum sensing etc., resulting in increased culture productivity of cells and metabolites.

Meanwhile, the upper limit of a carbon content in a liquid medium is not particularly limited. For example, the carbon content is preferably 100 g/L or less and more preferably 72 g/L or less.

In the present invention, a liquid medium that is preferably used for culturing has a C/N ratio (weight ratio of carbon content to nitrogen content) of 3 to 12.

The C/N ratio is calculated as follows: C/N ratio=sum of carbon contents in each medium component/sum of nitrogen contents in each medium component.

Other medium components, such as trace metal salts commonly used for culturing sporulating bacteria such as *Bacillus* bacteria, may be added as long as they do not adversely affect sporulation and productivity of target metabolites, and if necessary, amino acids or vitamins may be added, for example.

In the method of the present invention, a sporulation-inhibiting (delaying) substance is added into a medium and the sporulating bacteria are cultured. A sporulation-inhibiting substance may be any substance capable of inhibiting the sporulation of sporulating bacteria such as *Bacillus* bacteria, and examples thereof include enzyme inhibitors. Specifically, lincomycin, erythromycin, rifampicin, chloramphenicol, streptomycin, caffeine, caffeic acid, actinomycin, fusidic acid, lipiarmycin, puromycin, spectinomycin, tetracycline, and thiostreptone can be used.

Many of these inhibiting substances exhibit at certain concentrations the effect of inhibiting the growth of vegetative cells. However, when used at concentrations significantly lower than such concentrations, these inhibiting substances inhibit sporulation while exhibiting almost no effect of inhibiting the growth of vegetative cells.

In the method of the present invention, the concentration of a sporulation-inhibiting substance to be added to a medium is preferably the same as or lower than the growth-inhibiting concentration of the substance at which the growth of sporulating bacteria is inhibited, and is preferably 15 ppm or less, and more preferably 10 ppm or less, for example. Meanwhile, the lower limit of the concentration may be a concentration at which a sporulation-inhibiting substance can exhibit the effect of inhibiting sporulation, and is preferably 0.01 ppm or more.

For example, the concentration of lincomycin preferably ranges from 0.05 ppm to 15 ppm, further preferably 0.05 ppm to 1 ppm, and more preferably 0.05 ppm to 0.75 ppm. The concentration of erythromycin preferably ranges from 0.05 ppm to 1 ppm, the concentration of rifampicin preferably ranges from 5 ppm to 10 ppm, the concentration of chloramphenicol preferably ranges from 0.1 ppm to 2 ppm, the concentration of streptomycin preferably ranges from 5 ppm to 15 ppm, the concentration of caffeine preferably ranges from 5 ppm to 10 ppm, the concentration of caffeic acid preferably ranges from 5 ppm to 10 ppm, the concentration of actinomycin preferably ranges from 0.1 ppm to 10 ppm, the concentration of fusidic acid preferably ranges from 0.1 ppm to 10 ppm, the concentration of lipiarmycin preferably ranges from 0.1 ppm to 10 ppm, the concentration of puromycin preferably ranges from preferably ranges from 0.1 ppm to 10 ppm, the concentration of spectinomycin preferably ranges from 0.1 ppm to 10 ppm, the concentration of tetracycline preferably ranges from 0.1 ppm to 10 ppm, and the concentration of thiostreptone preferably ranges from 0.1 ppm to 10 ppm.

A sporulation-inhibiting substance may be contained in a medium at the start of culture or may be added during culture. When added during culture, the sporulation-inhibiting substance is preferably added at a timing in a time period of from 0 hour to ten hours after the start of culture, for example.

In the presence of a sporulation-inhibiting substance added, sporulating bacteria such as *Bacillus* bacteria are preferably cultured until the bacterial cell concentration reaches a high concentration such as $1\times10^8$/ml or more, and more specifically, preferably cultured for 5 to 80 hours.

The sporulation may be accelerated through long-time culture in the presence of a sporulation-inhibiting substance. For example, in the case of lincomycin, sporulation can be accelerated by 40 to 80 hours of culture after addition of 0.05 ppm to 0.5 ppm lincomycin. In the case of chloramphenicol, sporulation can be accelerated by 40 to 80 hours of culture after addition of 0.1 ppm to 0.5 ppm chloramphenicol. In the case of erythromycin, sporulation can be accelerated by 40 to 80 hours of culture after addition of 0.05 ppm to 0.2 ppm erythromycin.

In the method of the present invention, vegetative cells are cultured in such a manner that the concentration is high in the presence of a sporulation-inhibiting substance, and then a sporulation-accelerating substance may be added. Thus, sporulation can be accelerated.

Here, a sporulation-accelerating substance may be any substance capable of accelerating the sporulation of sporulating bacteria such as *Bacillus* bacteria, and examples thereof include nucleobase analogues, organic acids, amino acids, ammonium compounds, nitric acid compounds, nitrous acid compounds, and minerals. More specific examples thereof include decoyinine, mizoribine, mycophenol, 6-azauracil, lactic acid and a salt thereof, acetic acid and a salt thereof, butyric acid and a salt thereof, manganese, ammonium, calcium, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, ammonium lactate, and ammonium acetate.

It is effective to add a sporulation-accelerating substance during or after the growth of vegetative cells. Hence, a sporulation-accelerating substance is preferably added when the bacterial cell concentration is $1\times10^8$/ml or more. For example, a sporulation-accelerating substance is preferably added after 5 to 70 hours of culturing in the presence of a sporulation-inhibiting substance, and for example, a sporulation-accelerating substance is desirably added at a timing in a time period of from five hours to seventy hours after the start of culture.

By 10 to 30 hours of culturing in the presence of a sporulation-accelerating substance, a high concentration of spores can be obtained, for example.

Regarding the concentration of a sporulation-accelerating substance, for example, the concentration of decoyinine preferably ranges from 10 ppm to 1,000 ppm, the concentration of mizoribine preferably ranges from 10 ppm to 1,000 ppm, the concentration of mycophenol preferably ranges from 10 ppm to 1,000 ppm, the concentration of 6-azauracil preferably ranges from 10 ppm to 1,000 ppm, the concentration of lactic acid preferably ranges from 500 ppm to 10,000 ppm, the concentration of acetic acid preferably ranges from 500 ppm to 10,000 ppm, the concentration of butyric acid preferably ranges from 500 ppm to 10,000 ppm, the concentration of manganese preferably ranges from 100 ppm to 1,000 ppm, the concentration of ammonium preferably ranges from 500 ppm to 10,000 ppm, the concentration of calcium preferably ranges from 100 ppm to 1,000 ppm, the concentration of alanine preferably ranges from 500 ppm to 10,000 ppm, the concentration of arginine preferably ranges from 500 ppm to 10,000 ppm, the concentration of asparagine preferably ranges from 500 ppm to 10,000 ppm, the concentration of aspartic acid preferably ranges from 500 ppm to 10,000 ppm, the concentration of cysteine preferably ranges from 500 ppm to 10,000 ppm, the concentration of glutamine preferably ranges from 500 ppm to 10,000 ppm, the concentration of glutamic acid preferably ranges from 500 ppm to 10,000 ppm, the concentration of glycine preferably ranges from 500 ppm to 10,000 ppm, the concentration of histidine preferably ranges from 500 ppm to 10,000 ppm, the concentration of isoleucine preferably ranges from 500 ppm to 10,000 ppm, the concentration of leucine preferably ranges from 500 ppm to 10,000 ppm, the concentration of lysine preferably ranges from 500 ppm to 10,000 ppm, the concentration of methionine preferably ranges from 500 ppm to 10,000 ppm, the concentration of phenylalanine preferably ranges from 500 ppm to 10,000 ppm, the concentration of proline preferably ranges from 500 ppm to 10,000 ppm, the concentration of serine preferably ranges from 500 ppm to 10,000 ppm, the concentration of threonine preferably ranges from 500 ppm to 10,000 ppm, the concentration of tryptophan preferably ranges from 500 ppm to 10,000 ppm, the concentration of tyrosine preferably ranges from 500 ppm to 10,000 ppm, and the concentration of valine preferably ranges from 500 ppm to 10,000 ppm.

Various other conditions including culture vessels, medium compositions, concentrations, temperatures, pHs, and oxygen concentrations, etc., may be the conditions to be employed for general liquid culture of sporulating bacteria such as *Bacillus* bacteria. For example, bacteria are cultured at 20° C. to 40° C. under the aerobic conditions (e.g., oxygen concentration of 15% to 50%) with agitation. The pH of the medium preferably ranges from 6.5 to 8.5, and more preferably ranges from 7.0 to 8.0.

In this manner, cells of sporulating bacteria such as *Bacillus* bacteria having a high sporulation rate (e.g., 50% or more, preferably 80% or more) and metabolites of *Bacillus* bacteria can be obtained. Cells of sporulating bacteria such as *Bacillus* bacteria having such a high sporulation rate and metabolites of *Bacillus* bacteria can be used for desired purposes after adequate procedures such as condensation or removal, drying, and the like of the medium.

EXAMPLES

The present invention will be described in detail below with reference to Examples, but is not limited to the following Examples.

Example 1

<High-Concentration Growth (*Bacillus subtilis*) by Inhibition of Sporulation>

Using a 500 ml Erlenmeyer flask (with baffles), each 100 ml of media listed in Table 1 was prepared and then autoclave sterilization was carried out. Glucose was separately sterilized and aseptically mixed in order to avoid Maillard reaction.

The carbon contents of glucose, defatted soy flour, corn steep liquor, and a yeast extract among medium components were each calculated as 40% by weight of the total sugar amount and 50% by weight of the total protein amount. The total sugar amount was found by determining the reducing sugar concentration by Somogyi method after 2.5 hours of hydrolysis in acid at 100° C. The total protein amount was found by determining the total nitrogen amount by the Kjeldahl method, and then multiplying the amount by conversion factor, 6.25.

TABLE 1

Medium Composition

| Component | Manufacturer | Concentration (g/L) |
|---|---|---|
| Glucose | Wako Pure Chemicals | 12.500 |
| Defatted soy flour | Ajinomoto Healthy Supply | 10.000 |
| Corn steep liquor | Roquette | 2.500 |
| Yeast extract | Difco | 2.000 |
| $MnCl_2 \cdot 4H_2O$ | Wako Pure Chemicals | 0.090 |
| NaCl | Wako Pure Chemicals | 0.500 |
| $KH_2PO4$ | Wako Pure Chemicals | 0.250 |
| $MgSO_4 \cdot 7H_2O$ | Wako Pure Chemicals | 0.313 |
| $CaCl_2$ | Wako Pure Chemicals | 0.094 |
| $FeSO_4$ | Wako Pure Chemicals | 0.00019 |
| Carbon content | | 9.1 |
| Nitrogen content | | 1.1 |

Test sections were set as shown in Table 2. According to the conditions of each test section, the filter-sterilized aqueous solution of each sporulation-inhibiting substance was added aseptically to each medium. One loopful of *Bacillus subtilis* MBI-600 was taken from a colony grown on a nutrient agar medium, inoculated, and then cultured with shaking at 30° C. and 150 rpm for 64 hours.

Each of the thus obtained culture liquid was diluted 10-fold with sterile water, and then the bacterial cell concentration (vegetative cells and spores) and the sporulation rate (spore concentration/bacterial cell concentration) were measured using an optical microscope and a bacterial cell counter. The results are shown in Table 2.

TABLE 2

Test Result

| Test No. | Sporulation-inhibiting substance added | Concentration (ppm) | Bacterial cell concentration (/mL) | Sporulation rate | Spore concentration (/mL) |
|---|---|---|---|---|---|
| 1 | — | — | 3.2e+9 | 87% | 2.8e+9 |
| 2 | Lincomycin | 0.1 | 4.7e+9 | 100% | 4.7e+9 |
| 3 | Lincomycin | 1.0 | 7.0e+9 | 0% | — |
| 4 | Erythromycin | 0.1 | 3.5e+9 | 80% | 2.8e+9 |
| 5 | Erythromycin | 1.0 | 6.2e+9 | 0% | — |
| 6 | Streptomycin | 12.5 | 4.3e+9 | 100% | 4.3e+9 |
| 7 | Streptomycin | 15.0 | 5.5e+9 | 54% | 3.0e+9 |

The effect of inhibiting sporulation was not observed in the test section with the lincomycin concentration of 0.1 ppm, however, the effect of inhibiting sporulation was observed in the test section with the same of 1 ppm. Meanwhile, the bacterial cell concentrations tended to increase as the lincomycin concentrations increased.

Similarly, the effect of inhibiting sporulation was not observed in the test section with the erythromycin concentration of 0.1 ppm, however, the effect of inhibiting sporulation was observed in the test section with the same of 1 ppm. Moreover, the bacterial cell concentrations tended to increase as the erythromycin concentrations increased.

Furthermore, the effect of inhibiting sporulation was not observed in the test section with the streptomycin concentration of 12.5 ppm, however, the effect of inhibiting sporulation was observed in the test section with the same of 15.0 ppm. Meanwhile, the bacterial cell concentrations tended to increase as the streptomycin concentrations increased.

Example 2

<High-Concentration Growth of Vegetative Cells by Inhibition of Sporulation and High-Level Production of Spores (*Bacillus subtilis*) by Induction of Sporulation>

Using a 500 ml Erlenmeyer flask (with baffles), each 100 ml of media listed in Table 1 was prepared and then autoclave sterilization was carried out. Note that glucose was separately sterilized and aseptically mixed in order to avoid Maillard reaction.

Test sections were set as described in Table 3. According to the conditions of each test section, the filter-sterilized aqueous solution of each sporulation-inhibiting substance was added aseptically to each medium. According to the conditions of each test section, one loopful of *Bacillus subtilis* MBI-600 was taken from a colony grown on a nutrient agar medium, inoculated, and then cultured with shaking at 30° C. and 150 rpm.

Sixteen (16) hours after the start of culture, each sporulation-accelerating substance was added according to the conditions of each test section, culture was continued. Forty-five (45) hours after the start of culture, culture was stopped.

Each of the thus obtained culture liquid was diluted 10-fold with sterile water, and then the bacterial cell concentration (vegetative cells and spores) and the sporulation rate (spore concentration/bacterial cell concentration) were measured using an optical microscope and a bacterial cell counter. The results are shown in Table 3.

TABLE 3

| Test Result | | | | | | | |
|---|---|---|---|---|---|---|---|
| Test No. | Sporulation-inhibiting substance added | Concentration (ppm) | Sporulation-accelerating substance added | Concentration (ppm) | Bacterial cell concentration (/mL) | Sporulation rate | Spore concentration (/mL) |
| 1 | — | — | — | — | 3.2e+9 | 87% | 2.8e+9 |
| 2 | — | — | Ammonium lactate | 3,000 | 5.2e+9 | 91% | 4.8e+9 |
| 3 | — | — | Ammonium acetate | 3,000 | 4.6e+9 | 91% | 4.2e+9 |
| 4 | Lincomycin | 0.3 | — | — | 3.3e+9 | 80% | 2.7e+9 |
| 5 | Lincomycin | 0.5 | — | — | 4.4e+9 | 0% | — |
| 6 | Lincomycin | 1.0 | — | — | 5.1e+9 | 0% | — |
| 7 | Lincomycin | 2.0 | — | — | 5.9e+9 | 0% | — |
| 8 | Lincomycin | 0.3 | Ammonium lactate | 3,000 | 5.6e+9 | 91% | 5.1e+9 |
| 9 | Lincomycin | 0.5 | Ammonium lactate | 3,000 | 7.2e+9 | 79% | 5.7e+9 |
| 10 | Lincomycin | 0.5 | Ammonium acetate | 2,000 | 6.4e+9 | 64% | 4.1e+9 |
| 11 | Lincomycin | 0.5 | Ammonium acetate | 3,000 | 7.6e+9 | 71% | 5.4e+9 |
| 12 | Lincomycin | 0.5 | Ammonium acetate | 4,000 | 8.4e+9 | 72% | 6.1e+9 |
| 13 | Chloramphenicol | 1.4 | — | — | 5.4e+9 | 0% | — |
| 14 | Chloramphenicol | 1.4 | Decoyinine | 200 | 5.4e+9 | 76% | 4.1e+9 |

The effect of inhibiting sporulation was not observed in the test section with the lincomycin concentration of 0.3 ppm, however, the effect of inhibiting sporulation was observed in the test section with the same of 0.5 ppm or more. Moreover, the bacterial cell concentrations tended to increase as the lincomycin concentrations increased.

In the test sections in which ammonium lactate had been added as a sporulation-accelerating substance, improvement was observed in sporulation rate regardless of the lincomycin concentration, unlike test sections in which no such substance had been added. Particularly in the test sections with the lincomycin concentrations of 0.3 ppm and 0.5 ppm, in which ammonium lactate had been added, spore productivity was significantly higher than the same in the test sections in which no such substance had been added.

In the test sections with the lincomycin concentration of 0.5 ppm, in which ammonium acetate had been added, a tendency was observed such that the bacterial cell concentration and the sporulation rate increased as the amount of ammonium acetate added increased. Spore productivity was also significantly higher in all of these test sections than those of the test sections in which no such substance had been added.

In the test section with the chloramphenicol concentration of 1.4 ppm, the effect of inhibiting sporulation was observed. However, in the test section in which decoyinine had been added during culture in addition to chloramphenicol, improvement was observed in sporulation rate. Spore productivity was improved in both test sections more than that of the test sections in which no such substance had been added.

Example 3

<High-Concentration Growth of Vegetative Cells by Inhibition of Sporulation and High-Level Production of Spores (*Bacillus thuringiensis*)>

Using a 500 ml Erlenmeyer flask (with baffles), each 100 ml of media listed in Table 1 was prepared and then autoclave sterilization was carried out. Note that glucose was separately sterilized and aseptically mixed in order to avoid Maillard reaction.

Test sections were set as shown in Table 4. According to the conditions of each test section, the filter-sterilized aqueous solution of each sporulation-inhibiting substance was added aseptically to each medium. According to the conditions of each test section, one loopful of *Bacillus thuringiensis* NBRC 101235 strain was taken from a colony grown on a nutrient agar medium, inoculated, and then cultured with shaking at 30° C. and 150 rpm for 40 hours.

Each of the thus obtained culture liquid was diluted 10-fold with sterile water, and then the bacterial cell concentration (vegetative cells and spores) and the sporulation rate (spore concentration/bacterial cell concentration) were measured using an optical microscope and a bacterial cell counter. The results are shown in Table 4.

TABLE 4

| Test Result | | | | | |
|---|---|---|---|---|---|
| Test No. | Sporulation-inhibiting substance added | Concentration (ppm) | Bacterial cell concentration (/mL) | Sporulation rate | Spore concentration (/mL) |
| 1 | — | — | 1.0e+9 | 54% | 5e+8 |
| 2 | Lincomycin | 5.0 | 1.4e+9 | 86% | 1.2e+9 |
| 3 | Lincomycin | 10.0 | 1.4e+9 | 71% | 1.0e+9 |
| 4 | Lincomycin | 12.5 | 9e+8 | 13% | 1e+8 |
| 5 | Chloramphenicol | 2.0 | 1.6e+9 | 79% | 1.3e+9 |
| 6 | Chloramphenicol | 6.0 | 8e+6 | 0% | — |
| 7 | Erythromycin | 0.05 | 1.5e+9 | 73% | 1.1e+9 |
| 8 | Erythromycin | 0.1 | 2.0e+9 | 16% | 3e+8 |

The effect of inhibiting sporulation was confirmed in the test section with the lincomycin concentration of 12.5 ppm. On the other hand, in the test sections with the lincomycin concentrations of 10.0 ppm or lower, the bacterial cell concentration and the spore concentration tended to increase.

In the test section with the chloramphenicol concentration of 6.0 ppm, the growth and the effect of inhibiting sporulation were confirmed. On the other hand, in the test section with the same of 2.0 ppm, the bacterial cell concentration and the spore concentration tended to increase.

In the test section with the erythromycin concentration of 0.1 ppm, the effect of inhibiting sporulation was confirmed. On the other hand, in the test section with the same of 0.05 ppm, the bacterial cell concentration and the spore concentration tended to increase.

The bacterial cell concentration increased through the addition of a given amount of an antibiotic, and spore productivity improved through sufficient time (40 hours) of culturing without the addition of any sporulation-accelerating substance.

Example 4

<High-Level Production of Surfactin (*Bacillus subtilis*) by Inhibition of Sporulation>

Using a 500 ml Erlenmeyer flask (with baffles), each 100 ml of media listed in Table 5 was prepared and then autoclave sterilization was carried out. Note that glucose was separately sterilized and aseptically mixed in order to avoid Maillard reaction.

Test sections were set as shown in Table 6. According to the conditions of each test section, the filter-sterilized aqueous solution of each sporulation-inhibiting substance was added aseptically to each medium. According to the conditions of each test section, one loopful of *Bacillus subtilis* MBI-600 strain was taken from a colony grown on a nutrient agar medium, inoculated, and then cultured with shaking at 30° C. and 150 rpm.

TABLE 5

| Medium Composition | | |
|---|---|---|
| Component | Manufacturer | Concentration (g/L) |
| Glucose | Wako Pure Chemicals | 25.000 |
| Defatted soy flour | Ajinomoto Healthy Supply | 20.000 |
| Corn steep liquor | Difco | 5.000 |
| Yeast extract | Roquette | 4.000 |
| $MnCl_2 \cdot 4H_2O$ | Difco | 0.180 |
| NaCl | Wako Pure Chemicals | 1.000 |
| $KH_2PO4$ | Wako Pure Chemicals | 0.500 |
| $MgSO_4 \cdot 7H_2O$ | Wako Pure Chemicals | 0.625 |
| $CaCl_2$ | Wako Pure Chemicals | 0.188 |
| $FeSO_4$ | Wako Pure Chemicals | 0.00038 |
| Carbon content | | 18.2 |
| Nitrogen content | | 2.2 |

Fifty (50) hours after the start of culture, culture was stopped.

Each of the obtained cultured liquid was centrifuged using a refrigerated centrifuge (TOMY SEIKO Co., Ltd. MX-307) at 10,000 rpm and 20° C. for 30 minutes, thereby collecting a supernatant.

To a solid-phase extraction column (Nihon Waters K.K. Oasis HLB 3 cc (400 mg) LP Extraction Cartridge), 3 ml of 0.1% TFA-containing acetonitrile was added and allowed to pass therethrough, and then 3 ml of 0.1% TFA-containing distilled water was added to pass through the column. Two ml of the thus collected centrifugal supernatant of each culture medium was added to pass through the column, 6 ml of 0.1% TFA-containing distilled water, and then 3 ml of 0.1% TFA-containing acetonitrile/distilled water (20:80, v/v) were allowed to pass through the column in sequence for washing. Next, 3 ml of 0.1% TFA-containing acetonitrile/distilled water (90:10, v/v) was allowed to pass through the column, thereby collecting an eluate. 0.1% TFA-containing acetonitrile/distilled water (90:10, v/v) was added, so that the amount of the collected solution was 4 ml, and then HPLC analysis was conducted under the following conditions.

HPLC: Agilent Technologies, Inc. 1260 Infinity

Column: Nihon Waters K.K. XBridge C18 5 μm 4.6×250 mm

Mobile phase: A: 0.1% TFA-containing distilled water, B: 0.1% TFA-containing acetonitrile 0 to 5 minutes A 80%/B 20%

5 to 25 minutes A 80%/B 20%→B 100%

25 to 30 minutes B 100%

30 to 40 minutes A 80%/B 20%

Flow rate: 1 ml/min

Temperature: 40° C.

Detection: UV205 nm

Injection amount: 20 μL

Authentic sample: Surfactin Sodium Salt (Wako Pure Chemicals)

Concentration: 30 ppm, 120 ppm

Solvent: 0.1% TFA-containing acetonitrile/distilled water (90:10, v/v)

Each medium was compared with the authentic sample in terms of peak area detected at the elution time of 27.6 minutes and that of 28.4 minutes, thereby calculating the surfactin concentration in the culture medium.

Results are shown in Table 6.

TABLE 6

| Test Result | | | | | | |
|---|---|---|---|---|---|---|
| Test No. | Sporulation-inhibiting substance added | Concentration (ppm) | Bacterial cell concentration (/mL) | Sporulation rate | Spore concentration (/mL) | Surfactin concentration (ppm) |
| 1 | — | — | 5.8e+9 | 100% | 5.8e+9 | 38.4 |
| 2 | Erythromycin | 0.1 | 8.1e+9 | 99% | 8.0e+9 | 58.5 |
| 3 | Erythromycin | 0.2 | 6.9e+9 | 100% | 6.9e+9 | 75.7 |

In the test sections with the erythromycin concentrations of 0.1 ppm and 0.2 ppm, the spore concentration and the surfactin concentration tended to increase.

Through addition of a given amount of an antibiotic, not only the productivity of spores but also the productivity of surfactin as a useful substance improved.

The invention claimed is:

1. A method for culturing a sporulating bacterium, the method comprising:

culturing a sporulating bacterium in a medium to which a sporulation-inhibiting substance is added, wherein the medium has a carbon content of 9.1 g/L or more, wherein the sporulation-inhibiting substance is lincomycin in an amount of 0.1 to 0.3 ppm wherein the sporulating bacterium is a *Bacillus subtilis*, wherein the culturing step produces at least $2.8\times10^9$ spores per ml.

2. The method for culturing a sporulating bacterium according to claim 1, further comprising:

adding a sporulation-accelerating substance to the medium.

3. The method for culturing a sporulating bacterium according to claim 2, wherein the sporulation-accelerating substance is added to the medium at a timing in a time period of from five hours to seventy hours after the start of culture.

4. The method for culturing a sporulating bacterium according to claim 2, wherein the sporulation-accelerating substance is a nucleobase analogue, an organic acid, an amino acid, an ammonium compound, a nitric acid compound, a nitrous acid compound or a mineral.

5. The method for culturing a sporulating bacterium according to claim 2, wherein the sporulation-accelerating substance is at least one substance selected from the group consisting of decoyinine, mizoribine, mycophenol, 6-azauracil, lactic acid and a salt thereof, acetic acid, an acetic acid salt, butyric acid, a butyric acid salt, manganese, ammonium, calcium, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, ammonium lactate, and ammonium acetate.

6. The method for culturing a sporulating bacterium according to claim 2, wherein the sporulation-accelerating substance is added at a concentration of 10 ppm to 10,000 ppm to the medium.

7. A method, comprising producing a substance by the culturing method of claim 1.

8. The method according to claim 7, wherein the substance is a spore of the sporulating bacterium.

9. The method according to claim 7, wherein the substance is a metabolite of the sporulating bacterium.

10. The method according to claim 9, wherein the metabolite is a cyclic lipopeptide.

11. The method according to claim 10, wherein the cyclic lipopeptide is at least one cyclic lipopeptide selected from the group consisting of iturin, surfactin, plipastatin, fengycin, bacillomycin, lichenysin, kurstakin, mycosubtilin, colistin, fusaricidin, paenibacterin, polymyxin, and pumilacidin.

12. A method of maintaining vegetative growth of a sporulating bacteria, culturing a sporulating bacterium in a medium to which a sporulation-inhibiting substance is added, wherein the medium has a carbon content of 9.1 g/L or more, and the sporulating bacterium produces one or more metabolites during vegetative growth, wherein the sporulation-inhibiting substance is lincomycin in an amount of 0.1 to 3 ppm wherein the concentration of one or more metabolites from the sporulating bacteria is increased compared to the sporulating bacteria cultured in a medium that has a carbon content of less than 9.1 g/L, and wherein the sporulating bacterium is a *Bacillus subtilis*, wherein the culturing step produces at least $2.8\times10^9$ spores per ml.

13. The method according to claim 12, further comprising isolating the metabolites from the medium cultured.

14. A method for culturing a *Bacillus subtilis*, the method comprising:

culturing a *Bacillus subtilis* in a medium to which lincomycin is added in an amount of 0.3 to 0.5 ppm, wherein the medium has a carbon content of 9.1 g/L or more, and then adding a sporulation-accelerating substance to the medium wherein the sporulation-accelerating substance is at least one substance selected from the group consisting of ammonium lactate, and ammonium acetate in an amount of 2000 to 4000 ppm.

* * * * *